US011268963B2

(12) United States Patent
Emili (10) Patent No.: US 11,268,963 B2
(45) Date of Patent: Mar. 8, 2022

(54) PROTEIN SEQUENCING METHODS AND REAGENTS

(71) Applicants: THE GOVERNING COUNCIL OF THE UNIVERSITY OF TORONTO, Toronto (CA); Andrew Emili, Needham, MA (US)

(72) Inventor: Andrew Emili, Needham, MA (US)

( * ) Notice: Subject to any disclaimer, the term of this patent is extended or adjusted under 35 U.S.C. 154(b) by 553 days.

(21) Appl. No.: 15/768,602

(22) PCT Filed: Oct. 17, 2016

(86) PCT No.: PCT/CA2016/051204
§ 371 (c)(1),
(2) Date: Apr. 16, 2018

(87) PCT Pub. No.: WO2017/063093
PCT Pub. Date: Apr. 20, 2017

(65) Prior Publication Data
US 2018/0299460 A1    Oct. 18, 2018

Related U.S. Application Data

(60) Provisional application No. 62/242,619, filed on Oct. 16, 2015.

(51) Int. Cl.
| | |
|---|---|
| *G01N 31/00* | (2006.01) |
| *G01N 33/53* | (2006.01) |
| *G01N 33/68* | (2006.01) |
| *C07D 493/10* | (2006.01) |
| *C40B 20/04* | (2006.01) |

(52) U.S. Cl.
CPC ....... *G01N 33/6824* (2013.01); *C07D 493/10* (2013.01); *C40B 20/04* (2013.01); *Y02P 20/55* (2015.11)

(58) Field of Classification Search
None
See application file for complete search history.

(56) References Cited

U.S. PATENT DOCUMENTS

| | | | | |
|---|---|---|---|---|
| 9,566,335 | B1 * | 2/2017 | Emili | G01N 33/6824 |
| 10,481,162 | B2 * | 11/2019 | Emili | A61K 45/06 |
| 2014/0273004 | A1 * | 9/2014 | Havranek | C12Y 304/11018 435/7.1 |

FOREIGN PATENT DOCUMENTS

| | | |
|---|---|---|
| CA | 2745197 | 6/2010 |
| WO | 2007120805 | 10/2007 |
| WO | 2012178023 A1 | 12/2012 |
| WO | 2013112745 A1 | 8/2013 |
| WO | WO-2013112745 A1 * | 8/2013 ......... G01N 33/6818 |

OTHER PUBLICATIONS

Urano et al. Abstract(Optics in the Life Sciences, OSA Publishing, Optical Molecular probes, Imaging and Drug Delivery 2015, Vancouver Canada, Apr. 12-15, 2015). (Year: 2015).*
Urano et al. (Optics in the Life Sciences, OSA Publishing, Optical Molecular probes, Imaging and Drug Delivery 2015, Vancouver Canada, Apr. 12-15, 2015). (Year: 2015).*
Urano et al. Abstract (Optics in the Life Sciences, OSA Publishing, Optical Molecular probes, Imaging and Drug Delivery 2015, Vancouver Canada, Apr. 12-15, 2015). (Year: 2015) (Year: 2015).*
Chen, LH et al. "Effect of Linker for Immobilization of Glutathione on BSA-Assembled Controlled Pore Glass Beads", Bull, Korean Chem. Soc. 2004, vol. 25. No. 9 pp. 1366-1370.
Erbse, A et al., "ClpS is an essential component of the N-end rule pathway in *Escherichia coli*", Nature, vol. 439/9 Feb. 2006, pp. 753-756, doi: 10.1038/nature04412.
Fonovic, M. et al. Proteomics Evaluation of Chemically Cleavable Acitivty-based Probes, Molecular & Cellular Proteomics 6:1761-1770, 2007.
Guo, F. et al., "Crystal Structure of the Heterodimeric Complex of the Adaptor, ClpS, with the N-domain of the AAA+ Chaperone, ClpA*", The Journal of Biological Chemistry, vol. 277, No. 48, Issue of Nov. 29, pp. 46753-46763, 2002.
Holfok-Peters, Ch et al. "Enzymatic Cleavage Directly on the Probe Tip for Mass Spectrometic Identification of Peptides", Biomedical and Environmental Mass Spectrometry, vol. 19, pp. 159-163 (1990).
Harris T.D. et al., "Single-Molecule DNA Sequencing of a Viral Genome", Science 320, 106 (2008) DOI: 10.1126/science.1150427.
Henikoff, S. et al. "Amino acid substitution matrices from protein blocks", Proc. Natl. Acad. Sci. USA vol. 89, pp. 10915-10919, Nov. 1992 Biochemistry.
Ray, A et al., "Peptide nucleic acid (PNA): its medical and biotechnical applications and promise for the future", The FASEB journal vol. 14, Jun. 2000, pp. 1041-1060.
Okiyama, N. et al., "An automated fluorescence protein sequencer using 7-methylthio-4-(2,1,3-benzoxadiazolyl) isothiocyanate (MTBD-NCS) as an Edman reagent", Biomedical Chromatography 16: pp. 183-186 (2002). DOI: 10.1002/bmc124.
Roman-Hernandez, G. et al., "Molecular basis of substrate selection by the N-end rule adaptor protein ClpS ", PNAS Jun. 2, 2009, vol. 106, No. 22, pp. 8888-8893.
Schuenemann, V.J. et al., "Structural basis of N-end rule substrate recognition in *Escherichia coli* by the ClpAP adaptor protein ClpS" EMBO reports vol. 10, No. 5, 2009, pp. 508-514.
Stahl, P.J. et al., "On-the-Resin N-Terminal Modification of Long Synthetic Peptides" Anal Biochem. May 15, 2012; 424(2); 137-139 doi: 10.1016/j.ab2012 02.032.

(Continued)

*Primary Examiner* — Lisa V Cook (57) ABSTRACT

Described are optical methods and reagents for sequencing polypeptides. A probe that exhibits different spectral properties when conjugated to different N-terminal amino acids is conjugated to the N-terminal amino acid of a polypeptide. Sequentially detecting one or more spectral properties of the probe conjugated to the N-terminal amino acid and cleaving the N-terminal amino acid produces sequence information of the polypeptide. The use of super-resolution microscopy allows for the massively parallel sequencing of individual polypeptide molecules in situ such as within a cell. Also described are probes comprising hydroxymethyl rhodamine green, an isothiocyanate group and a protecting group.

20 Claims, 6 Drawing Sheets

Specification includes a Sequence Listing.

(56) References Cited

OTHER PUBLICATIONS

Tasaki, T et. al. "The Substrate Recognition Domains of the N-end Rule Pathway", Journal of Biological Chemistry, vol. 284, No. 3, Jan. 16, 2009, pp. 1884-1895.
Uno, S-n. et al., "A spontaneously blinking fluorophore based on intramolecular spirocyclization for live-cell super-resolution imaging", Nature Chemistry published online Jul. 10, 2014/ DOI:10.1038/NCHEM.2002.
Wang, K. H. et al., "The Molecular Basis of N-End Rule Recognition" Molecular Cell 32, 406-414, Nov. 7, 2008 pp. 406-414.
PCT/CA2016/051204 Written Opinion and International Search Report dated Dec. 22, 2016.
Zhang, Z. et al., "Ultrahigh-throughput single-molecule spectroscopy and spectrally resolved super-resolution microscopy" Nature Methods, NPG 2015 Nature America, Inc. doi: 10/1038/nmeth.3528.
Swaminathan, J., et al., "A Theoretical Justification for Single Molecule Peptide Sequencing." PLOS Computational Biology, Feb. 25, 2015, vol. 11, No. 2, pp. 1-17.
Kiuchi, T., et al., "Multitarget super-resolution microscopy with high-density labeling by exchangeable probes." Nature Methods, Jan. 1, 2015, vol. 12, No. 8, pp. 743-746.
Supplementary European Search Report completed Apr. 30, 2019 for corresponding European Patent Application No. 16854691.

\* cited by examiner

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa Ala Gly Trp Tyr Met Arg Leu Gly
1               5

PROTEIN SEQUENCING METHODS AND REAGENTS

RELATED APPLICATIONS

This application is a national phase entry of PCT/CA2016/051204 filed Oct. 17, 2016 (which designates the U.S.) which claims the benefit of priority of U.S. Provisional Patent Application No. 62/242,619 filed Oct. 16, 2015, the contents of which are hereby incorporated by reference.

INCORPORATION OF SEQUENCE LISTING

A computer readable form of the Sequence Listing "13795-P49671US01 SequenceListing.txt" (4,096 bytes), submitted via EFS-WEB and created on Apr. 13, 2018, is herein incorporated by reference.

FIELD OF THE INVENTION

This invention relates to the field of protein sequencing and more specifically to methods, assays and reagents for sequencing protein or polypeptide molecules as well as to fluorescent single molecule imaging methods, assays and reagents for sequencing individual polypeptide molecules.

BACKGROUND OF THE INVENTION

Proteins underlie virtually every biological process; perturbations in their expression, degradation, interactions, or localization are associated with disease. Yet while methods for protein identification, quantification and imaging are needed throughout biomedicine, existing techniques have serious constraints.

Historically (1960-90s), protein sequencing was based on Edman degradation, which involves the sequential chemical modification of the N-terminal amino acid from an immobilized polypeptide population with a reactive isothiocyanate-based reporter reagent and their subsequent cleavage and detection by differential chromatography. While automatable, the technology has low sensitivity and is not applicable to heterogeneous samples (i.e. mixtures of different polypeptides), limiting utility. Over the last 20 years, mass spectrometry has emerged as a preferred technology for identifying proteins in biological specimens (i.e. complex mixtures). Yet it also suffers from limited dynamic range, biased detection, and incremental performance gains. Moreover, it is based on ensemble measurements (bulk analysis), resulting in the loss of valuable contextual information (e.g. protein subcellular localization etc.).

Like mass spectrometry, fluorescent microscopy has a long and distinguished track record in the analyses of cellular proteins. Historically, while spatial resolution was limited by the wavelength of light, recently introduced super-resolution microscopy techniques based on single-molecule localization have now overcome fundamental diffraction limits. Some of these new methods, like STORM (stochastic optical reconstruction microscopy), involve switching a sparse subset of fluorescent molecules on and off (dark vs. activated states) followed by image acquisition to allow for very precise probe localization (<20 nm in lateral plane). Crucially, however, these methods depend on the availability of fluorescent antibodies, or other similarly labeled affinity capture reagents such as aptamers, which are physically large relative to most cellular polypeptides, diminishing resolution, and/or which may bind cellular proteins in addition to the target of interest, producing artifacts, and typically fewer than 3-4 different cellular proteins can be imaged together at one time.

There remains a need for novel methods and assays for sequencing single polypeptide molecules and for identification, quantification and imaging of many different proteins simultaneously in complex biological samples.

SUMMARY OF THE INVENTION

In a broad aspect, the disclosure provides a method for sequencing a polypeptide wherein the N-terminal amino acid of the polypeptide is conjugated to a probe that exhibits different spectral properties when conjugated to different N-terminal amino acids. In one embodiment, the probe is an optically active reporter probe, such as a fluorescent dye.

As set out in the Examples, small but characteristic differences in spectral properties observed after conjugation of a probe to different amino acids may be used to infer the identity of the corresponding N-terminal amino acid residue. Furthermore, the use of single molecule imaging techniques that allow for the detection of spectral properties for spatially resolved individual molecules, such as but not limited to super-resolution microscopy, may be used for the parallel sequencing of large numbers of polypeptides in vitro or in situ, such as on or in tissues, cells, lipid membranes or organelles. The methods described herein can therefore also be used to obtain information on protein identity, quantity and subcellular location within a biological or environmental sample.

Accordingly, in one embodiment there is provided a method of sequencing a polypeptide comprising:

a) conjugating a probe to an N-terminal amino acid of the polypeptide wherein the probe exhibits different spectral properties when conjugated to different N-terminal amino acids;

b) detecting one or more spectral properties of the probe conjugated to the N-terminal amino acid;

c) identifying the corresponding N-terminal amino acid of the polypeptide by comparing the spectral properties of the probe to a plurality of reference spectral properties, wherein each reference spectral property is representative of the probe conjugated to a different N-terminal amino acid;

d) cleaving the N-terminal amino acid of the polypeptide; and e) repeating steps (a) to (d) to determine the sequence of at least a portion of the polypeptide.

In one embodiment, the polypeptide is a single polypeptide molecule.

In one embodiment, the probe is covalently conjugated to the N-terminal amino acid of the polypeptide.

In one embodiment, the probe is an optical reporter probe, such as a fluorescent dye. In one embodiment, detecting one or more spectral properties of the probe conjugated to the N-terminal amino acid comprises detecting the fluorescence emission of the probe bound to the N-terminal amino acid of the polypeptide at one or a plurality of wavelengths. In one embodiment, detecting one or more spectral properties of the probe conjugated to the N-terminal amino acid comprises detecting an emission intensity, polarity/anisotropy or lifetime. In one embodiment, the probe comprises a fluorescent moiety. In one embodiment, the fluorescent moiety is a xanthene derivative, such as a dye based on fluorescein, eosin, or rhodamine. In one embodiment, the probe comprises rhodamine green, or a derivative thereof. In one embodiment, the probe is hydroxymethyl rhodamine green (HMRG)-BOC-ITC).

In one embodiment, the probe comprises a spontaneously blinking dye or a photoswitchable dye. In one embodiment, the probe comprises a reactive/labile isothiocyanate group.

In one embodiment, the N-terminal amino acid of the polypeptide or N-terminal amino acid derivative of the polypeptide is cleaved using Edman chemical degradation.

In one embodiment, methods described herein can be used to sequence a polypeptide in situ. For example in one embodiment the polypeptide is in or on a biological sample, such as a tissue, cell, lipid membrane or intracellular organelle, or sample thereof. In another embodiment, the polypeptide is conjugated to substrate prior to conjugating the probe to the N-terminal amino acid. In one embodiment, the C-terminal end of the polypeptide is conjugated to a substrate, optionally through a linker.

In one aspect, the methods described herein may be used to sequence a plurality of polypeptides in parallel. For example, in one embodiment, the method comprises conjugating a plurality of probes to the N-terminal amino acid of each of the plurality of polypeptides, detecting one or more spectral properties for each probe conjugated to the N-terminal amino acid of each of the plurality of polypeptides, and identifying the N-terminal amino acid of each of the plurality of polypeptides by comparing the plurality of spectra properties to a plurality of reference (standard) spectral properties.

In one embodiment, the methods described herein comprise detecting one or more spectral properties for each probe conjugated to the N-terminal amino acid of each of the plurality of polypeptides at spatially resolved locations in a sample containing the plurality of polypeptides. For example, in one embodiment, the methods described herein include detecting one or more spectral properties of a probe using super resolution microscopy, optionally stochastic optical reconstruction microscopy (STORM) or related/derivative methods.

In one embodiment, the methods described herein include obtaining a fluorescence emission spectra of the probe conjugated to the N-terminal amino acid and comparing the fluorescence emission spectra to a plurality of reference spectra, wherein each reference spectra is representative of the probe conjugated to a different N-terminal amino acid.

In one embodiment, the method comprises comparing the spectral properties of the probe conjugated to an N-terminal amino acid to one or a plurality of reference spectral properties. In one embodiment, each reference spectral property is representative of the probe conjugated to a different N-terminal amino acid. In one embodiment, comparing the spectral properties of the probe to a plurality of reference spectral properties comprises the use of machine learning, genetic algorithms, or principle component analysis (PCA).

The methods described herein may be used in combination with available polypeptide sequence information or databases in order to predict the sequence of a polypeptide. For example, in one embodiment the method comprises comparing the sequence of at least one polypeptide molecule determined using a probe as described herein to a reference protein sequence database.

Also provided are reagents and probes such as fluorescent optical reporter probes useful for the method of sequencing a polypeptide as described herein. In one embodiment, the probe exhibits different spectral properties when conjugated to different N-terminal amino acids, such as different emission intensity, polarity/anisotropy or lifetime. In one embodiment, the probe exhibits a different spectral shape when conjugated to different N-terminal amino acids.

In one embodiment, the probe comprises a synthetic fluorescent dye. In one embodiment, the probe comprises a xanthene derivative, such as a dye based on fluorescein, eosin, or rhodamine. For example, in one embodiment, the probe comprises hydroxymethyl rhodamine green (HMRG). In one embodiment, the probe is suitable for optical detection using super-resolution microscopy. In one embodiment, the probe is a spontaneously blinking dye or a photoswitchable dye. In one embodiment, the probe is facilitates the chemical cleavage of the N-terminal amino acid from the polypeptide. For example, in some embodiment the probe comprises a reactive isothiocyanate (ITC) group.

In one embodiment, there is provided a chemical compound comprising a reactive ITC group, HMRG and a protecting group (PG) such as tert-Butyloxycarbonyl (BOC).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

The present description provides molecular imaging-based methods, assays and reagents useful for sequencing proteins. In one aspect, the methods and reagents are useful for sequencing single polypeptide molecules, multiple molecules of a single polypeptide, or multiple different single polypeptide molecules. In one aspect, the methods and reagents are useful for determining the N-terminal amino acid of one or more polypeptides. In one aspect, the methods are useful for the simultaneous sequencing of a plurality of polypeptide molecules, such as for massively parallel sequencing techniques. Accordingly samples comprising a mixture of different proteins, or peptides, can be assayed according to the methods described herein to generate (partial or complete) sequence information regarding individual protein molecules in the sample. In a further aspect, the methods are useful for protein expression profiling in biological samples containing complex protein mixtures such as cells. For example, the methods are useful for generating both quantitative (frequency) and qualitative (sequence) data for proteins contained in a sample. In addition, the methods and reagents described herein are useful for generating data on the location and/or distribution of proteins within a sample, such as biological sample or environmental sample.

The inventor has determined that differences in the spectral properties of a probe conjugated to the N-terminal amino acid residue of a polypeptide can be used to determine the identity of the 20+ naturally occurring N-terminal amino acid residues. As shown in Example 3 and FIG. 5, the spectra of a xanthene-based dye (HMRG-BOC) conjugated to different N-terminal amino acids of a test polypeptide (SEQ ID NO: 1) exhibited different spectral signatures allowing for the identification of the N-terminal amino acid of a polypeptide based on the spectra. In one embodiment, the methods and reagents described herein can be used to generate sequence information by sequentially identifying and then cleaving off the N-terminal amino acid of a polypeptide.

Accordingly, in one aspect there is provided a method of sequencing a polypeptide comprising conjugating a probe to an N-terminal amino acid of the polypeptide wherein the probe exhibits different spectral properties when conjugated to different N-terminal amino acids. In one embodiment, the probe is an optical reporter probe such as a fluorescent dye. In one embodiment, the method comprises detecting one or more spectral properties of the probe conjugated to the N-terminal amino acid. In one embodiment, the method comprises identifying the N-terminal amino acid of the polypeptide by comparing the spectral properties of the probe to a plurality of reference spectral properties, wherein each reference spectral property is representative of the probe conjugated to a different N-terminal amino acid. In one embodiment, the method comprises repeatedly cleaving off the N-terminal amino acid of the polypeptide, either chemically or enzymatically, then conjugating the newly exposed N-terminal amino acid to the probe and detecting one or more spectral properties of the conjugated probe in order to sequentially identify the consecutive amino acid sequence of the polypeptide.

As used herein, "polypeptide" refers to two or more amino acids linked together by a peptide bond. The term "polypeptide" includes proteins, or protein digests, that have a C-terminal end and an N-terminal end as generally known in the art and may be synthetic in origin or naturally occurring. As used herein "at least a portion of the polypeptide" refers to 2 or more amino acids of the polypeptide. Optionally, a portion of the polypeptide includes at least: 5, 10, 20, 30 or 50 amino acids, either consecutive or with gaps, of the complete amino acid sequence of the polypeptide, or the full amino acid sequence of the polypeptide.

The phrase "N-terminal amino acid" refers to an amino acid that has a free amine group and is only linked to one other amino acid by a peptide amide bond in the polypeptide. Optionally, the "N-terminal amino acid" may be an "N-terminal amino acid derivative". As used herein, an "N-terminal amino acid derivative" refers to an N-terminal amino acid residue that has been chemically modified, for example by an Edman reagent or other chemical in vitro or inside a cell via a natural post-translational modification (e.g. phosphorylation) mechanism.

As used herein, "sequencing a polypeptide" refers to determining the amino acid sequence of a polypeptide. The term also refers to determining the sequence of a segment of a polypeptide or determining partial sequence information for a polypeptide.

As used herein "the cleaving the N-terminal amino acid of the polypeptide" refers to a chemical or enzymatic reaction whereby the N-terminal amino acid or N-terminal amino acid derivative is removed from the polypeptide while the remainder of the polypeptide remains intact.

As used herein the term "sample" includes any material that contains one or more polypeptides. The sample may be a biological sample, such as animal or plant tissues, biopsies, organs, cells, membrane vesicles, plasma membranes, organelles, cell extracts, secretions, urine or mucous, tissue extracts or other biological specimens both natural or synthetic in origin. The term sample also includes single cells, organelles or intracellular materials isolated from a biological specimen, or viruses, bacteria, fungus or isolates therefrom. The sample may also be an environmental sample, such as a water sample or soil sample, or a sample of any artificial or natural material that contains one or more polypeptides.

Without being limited by theory, it is believed that the atomic interactions induced by different amino acid side-chains affect the electronic (ground or activation) states of the probe conjugated to a particular amino acid residue. In one embodiment, the probe is covalently conjugated to the N-terminal amino acid of the polypeptide.

Figure 5:
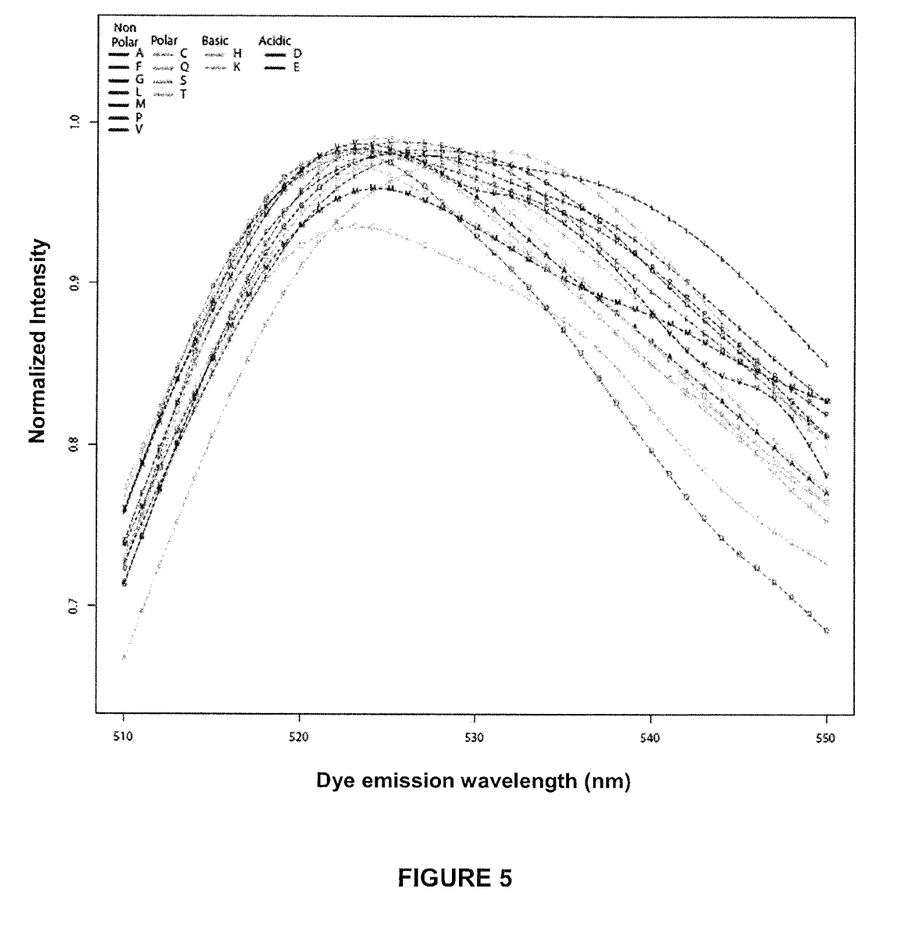
FIG. 5 shows the spectra of HMRG-BOC-ITC conjugated to a test polypeptide XAGWYMRLG (SEQ ID NO: 1; wherein X is any amino acid) having different N-terminal amino acids. The spectra of the polypeptides having different N-terminal amino acids are readily distinguished.
Figure 6:
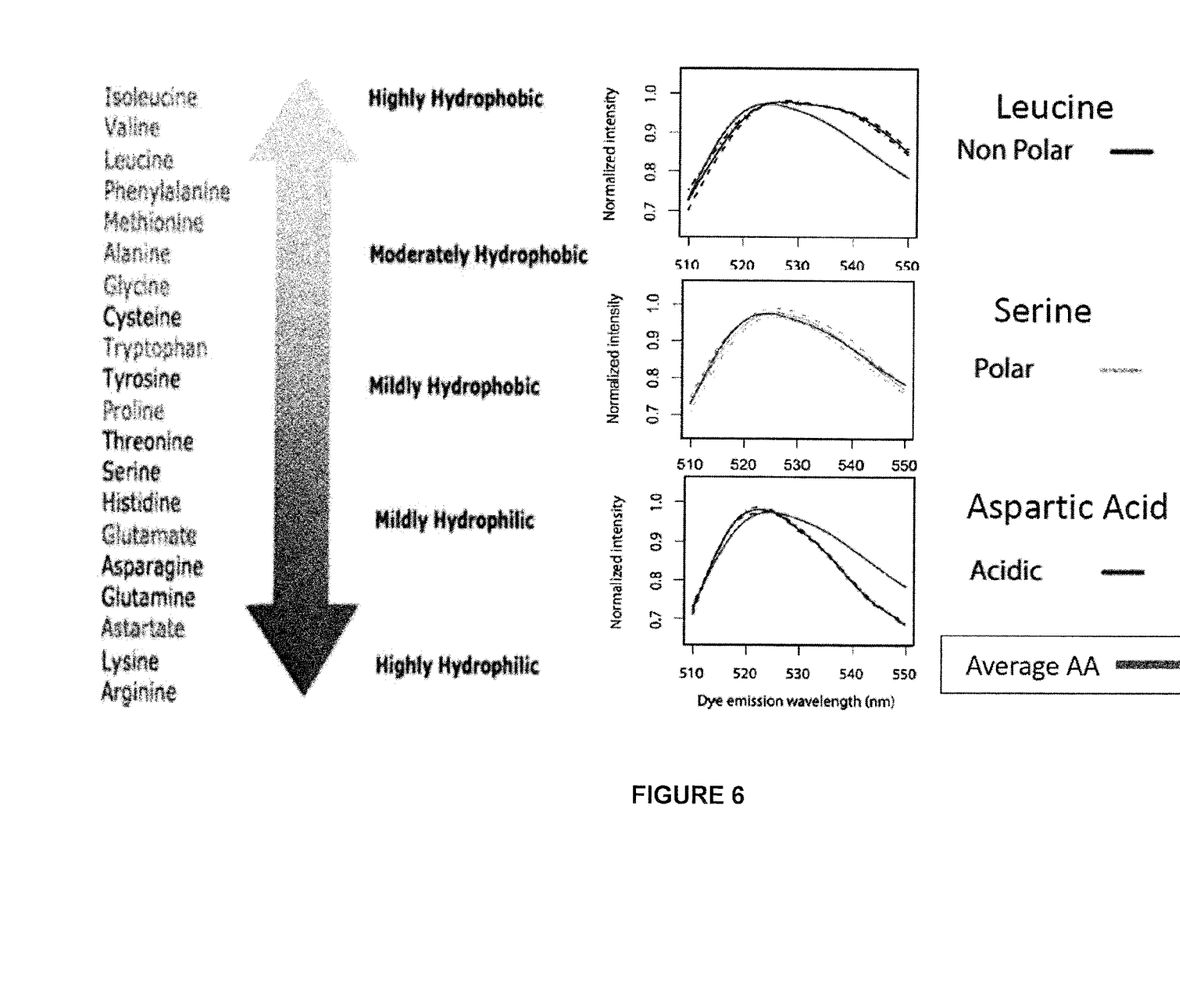
FIG. 6 shows that the spectra of HMRG-BOC-ITC coupled to hydrophobic N-terminal amino acids (such as Leucine) generally exhibit a red-shift relative to the average spectra of each of the 20 amino acids tested. The spectra of HMRG-BOC-ITC coupled to hydrophilic N-terminal amino acids (such as Aspartic Acid) generally exhibit a blue-shift relative to the average spectra of each of the 20 amino acids tested.

In one embodiment, these changes to the electronic (ground or activation) state of the probe conjugated to the N-terminal acid residue are detected by detecting changes to one or more spectral properties of the probe conjugated to the N-terminal amino acid residue, such as emission intensity, polarity/anisotropy or lifetime. As used herein, the term "spectral properties" refers to a detectable change in the emission intensity, polarity/anisotropy or lifetime at a single wavelength or at a plurality of wavelengths of a probe conjugated to an N-terminal amino acid relative to one or more different N-terminal amino acids. For example, in one embodiment spectral properties may include spectral shape or peak intensity and/or polarity. In one embodiment, the methods described herein include detecting fluorescence of the probe bound to the N-terminal amino acid of the polypeptide. As shown in FIG. 5, the fluorescent spectra of the xanthene-based probe HMRG-BOC conjugated to different N-terminal amino acids of a test polypeptide exhibited distinctive spectral properties. Comparing the spectra of can therefore be used to identify the N-terminal amino acid to which the probe is conjugated. As shown in FIG. 6, HMRG-BOC conjugated to hydrophobic N-terminal amino acids tends to exhibit a red-shift in fluorescent intensity compared to the average of all 20 amino acids while HMRG-BOC conjugated to hydrophilic N-terminal amino acids tends to exhibit a blue-shift in fluorescent intensity compared to the average of all 20 amino acids. Optionally, the methods described herein include comparing multiple spectral properties (e.g. spectral shape and polarity) between an N-terminal amino acid-probe conjugate and one or more controls in order to identify the identity of the N-terminal amino acid.

In one embodiment, the methods described herein comprise detecting the fluorescence emission intensity, polarity/anisotropy or lifetime at a single wavelength or at a plurality of wavelengths.

Figure 2:
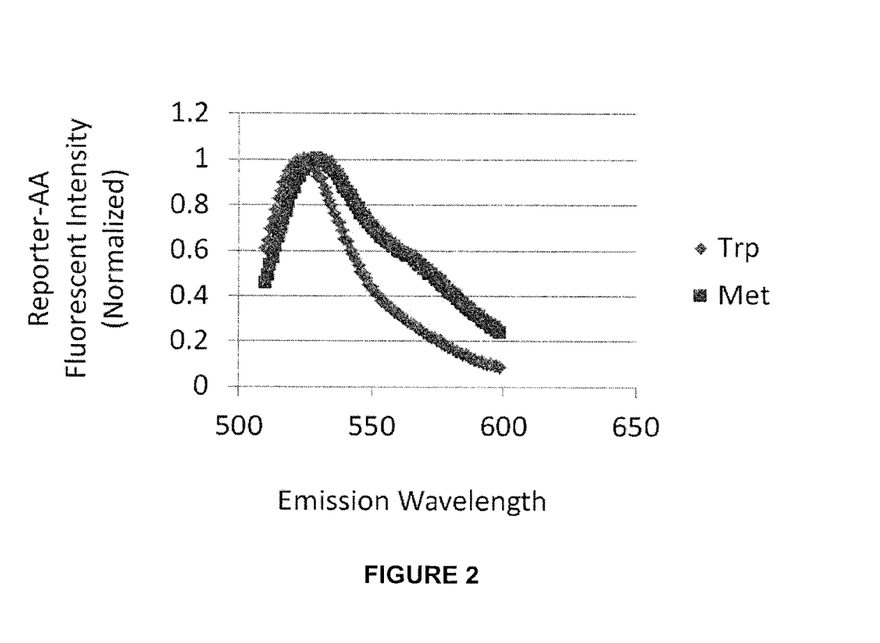
FIG. 2 shows the different fluorescence emission profiles of HMRG coupled to Methionine (Met) vs. Tryptophan (Trp) in solution at pH 5.
Figure 3:
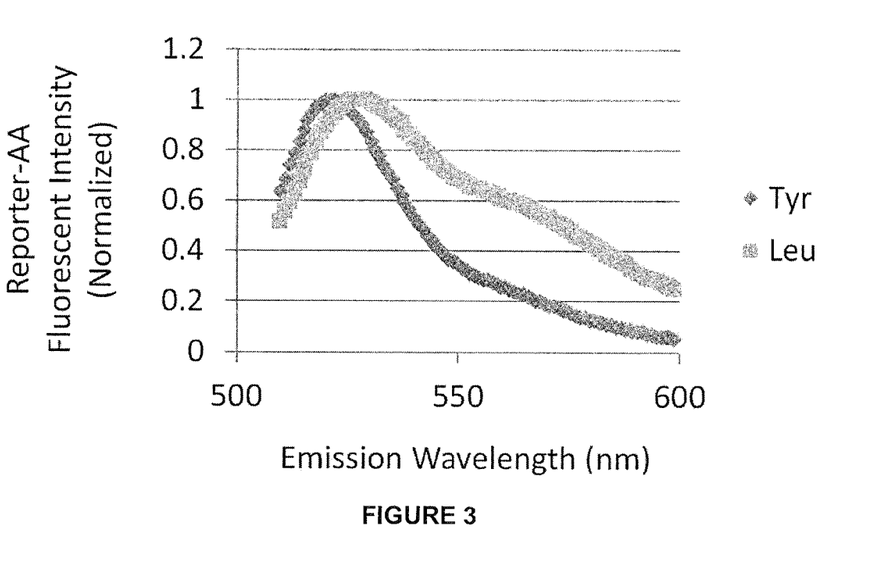
FIG. 3 shows the different fluorescence emission profiles of HMRG coupled to Tyrosine (Tyr) vs. Leucine (Leu) in solution at pH 5.

For example, in one embodiment, the methods described herein include detecting a fluorescent emission spectra for a probe conjugated to an amino acid residue, such as those shown in FIG. 2 or 3.

In one embodiment, the probes described herein exhibit different spectral properties when conjugated to different N-terminal amino acids. For example, various fluorescent dyes known in the art may be tested to identity those that exhibit unique spectral properties when conjugated to different amino acid residues.

In one embodiment, the probe comprises a xanthene derivative. For example, in one embodiment the probe is a fluorescein, eosin, or rhodamine derivative. For instance, in one embodiment, the fluorescent probe is a derivative of hydroxymethyl rhodamine green (HMRG). As shown in the Examples and FIG. 2, HMRG exhibits different spectral properties when conjugated to either Methionine or Tryptophan (or other amino acids). Similarly, FIG. 3 demonstrates different spectral properties of HMRG conjugated to Leucine or Tryptophan.

In one embodiment, the probe comprises an organic dye suitable for use with single molecule optical detection techniques. For example, in one embodiment the probe comprises a spontaneously blinking dye or a photoswtichable dye.

In one embodiment, the probe facilitates cleavage of the N-terminal amino acid from the polypeptide. For example, in one embodiment the probe comprises a reactive and labile isothiocyanate group.

In one embodiment, there is provided a compound comprising a hydroxymethyl rhodamine green (HMRG) derivative, a labile isothiocyanate group and a protecting group (PG) protecting the amine group on the opposite side of the xanthene moiety. In one embodiment, the compound has the formula:

The term "protecting group" or "PG" as used herein refers to a chemical moiety which protects or masks a reactive portion of a molecule to prevent side reactions in that reactive portion of the molecule, while manipulating or reacting a different portion of the molecule. After the manipulation or reaction is complete, the protecting group is removed under conditions that do not degrade or decompose the remaining portions of the molecule; i.e. the protected reactive portion of the molecule is "deprotected". The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas). Examples of protecting groups include, but are not limited to t-Boc, $C_{1-6}$acyl, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like. In one embodiment, the protecting group is an amine protecting group.

Figure 4A:
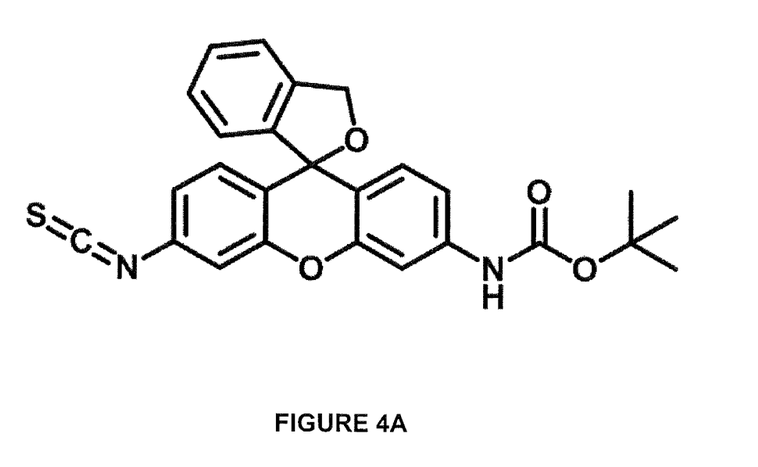
FIG. 4A shows the chemical structure of the probe HMRG-BOC-ITC.
Figure 4B:
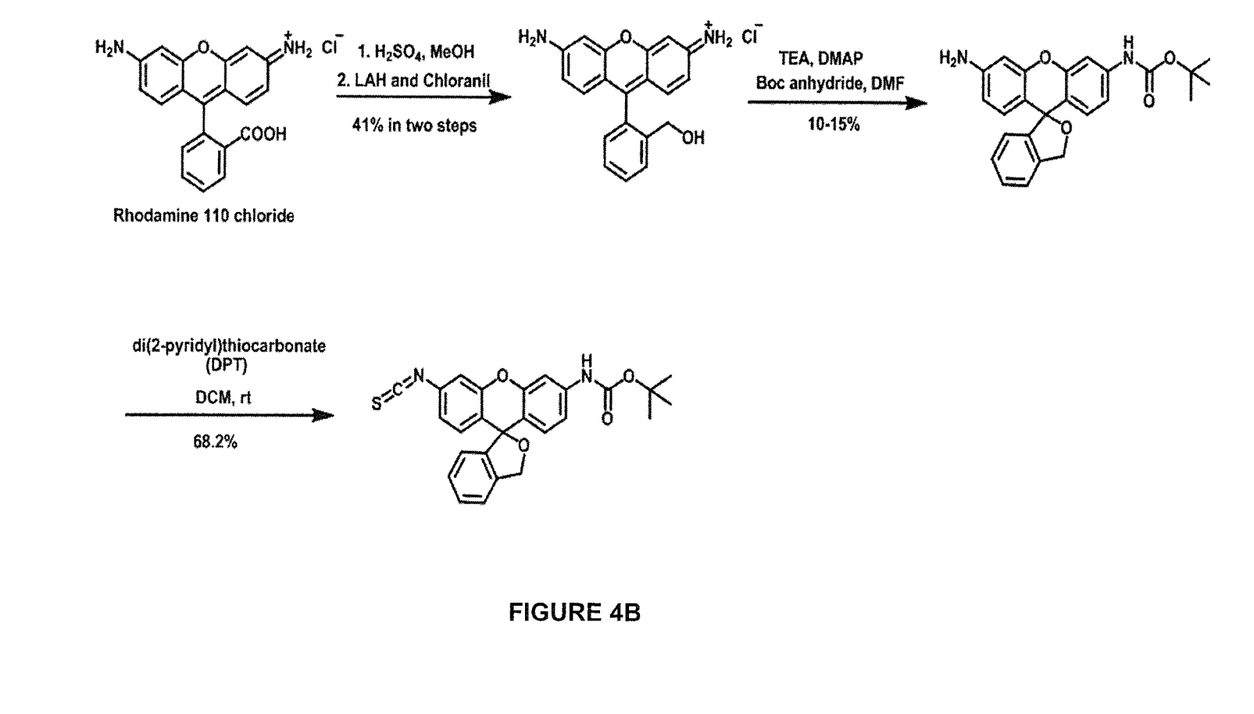
FIG. 4B shows a synthetic scheme for generating HMRG-Boc-ITC.

In one embodiment, the compound is HMRG-BOC-ITC as shown in FIG. 4A. An exemplary scheme for synthesizing HMRG-BOC-ITC is shown in FIG. 4B. Also provided is a method for synthesizing the compound HMRG-BOC-ITC as shown in FIG. 4B.

Optionally, in some embodiments the N-terminal amino acid of the polypeptide may be derivatized prior to conjugating the probe to the N-terminal amino acid. For example, in one embodiment the N-terminal amino acid is derivatized with an Edman reagent such as phenyl isothiocyanate (PITC).

In one embodiment, the methods described herein include cleaving the N-terminal amino acid or N-terminal amino acid derivative of the polypeptide using Edman, or related, chemical degradation. In one embodiment, the methods described herein include cleaving the N-terminal amino acid or N-terminal amino acid derivative enzymatically with a protease, for example an aminopeptidase.

In one embodiment, the methods described herein include comparing the spectral properties of the probe bound to an N-terminal amino acid of a polypeptide to a plurality of reference spectral properties. In one embodiment, each reference spectral property is representative of the probe conjugated to a different N-terminal amino acid. In one embodiment, comparing the spectral properties of the probe to the plurality of reference spectral properties comprises comparing the spectra of the probe bound to the N-terminal amino acid to a plurality of reference spectra. In one embodiment, the reference spectra are spectra of the probe bound to known N-terminal amino acids, such as the spectra shown in FIG. 5. In one embodiment, the method comprises identifying the closest match between the spectra of the probe and the reference spectra, thereby identifying the N-terminal amino acid of the polypeptide.

Various statistical methods known in the art may be used to compare the spectra of the probe and reference spectra in order to identify the closest match and the N-terminal amino acid of the polypeptide.

In one embodiment, suitable methods generate a quantitative measure of similarity or difference between the spectra and the reference spectra. In one embodiment, the methods described herein further comprises generating a statistical measure or probability score that a spectra is indicative of the presence of a particular N-terminal amino acid residue conjugated to the probe. In one embodiment, the methods used herein for comparing the spectral properties of an N-terminal amino acid-probe conjugate and a reference/control conjugate use one or more probabilistic algorithms. For example, a probabilistic algorithm can be trained to identify different N-terminal amino acids conjugated to HMRG-BOC using the spectral data provided in FIG. 5 associating specific spectra with specific N-terminal amino acids. Additional reference data sets suitable for training probabilistic algorithms can also be generated using other probes that exhibit different spectral properties when conjugated to different N-terminal amino acids. In one embodiment, machine learning, genetic algorithms, or principle component analysis (PCA) may be used for comparing spectra and reference spectra.

In another aspect, the methods and reagents described herein are useful for labeling and sequencing a plurality of polypeptides in parallel. For example, in one embodiment the methods described herein include conjugating a plurality of probe molecules to the N-terminal amino acid of each of the plurality of polypeptide molecules. In one embodiment, the method comprises detecting one or more spectral properties for each probe conjugated to the N-terminal amino acid of each of the plurality of polypeptides. The N-terminal amino acid of each of the plurality of polypeptides can then be identified by comparing the plurality of spectra properties to a plurality of reference (standards) spectral properties.

In one embodiment, the method comprises detecting one or more spectral properties for each probe conjugated to the N-terminal amino acid of each of the plurality of polypeptides at spatially resolved locations in a sample.

Different techniques known in the art may be used to detect spectral properties of different molecules at spatially resolved locations. For example, super resolution microscopy may be used to detect one or more spectral properties of a probe conjugated to the N-terminal amino acid at a particular location within a sample. In one embodiment, the methods described herein use stochastic optical reconstruction microscopy (STORM).

In one embodiment, the detecting the spectra properties of a probe includes ultrasensitive detection systems that are able to repeatedly detect signals from precisely the same co-ordinates in a sample, thereby assigning the detected spectral information to a unique polypeptide molecule.

In one embodiment, the spectral properties are detected using an optical detection system. Optical detection systems include a charge-coupled device (CCD), electron multiplying CCD (EMCCD), near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, total internal reflection fluorescence (TIRF) microscopy, super-resolution fluorescence microscopy, single-molecule localization microscopy, and single-molecule spectroscopy. In general, methods involve detection of laser-activated fluorescence using a microscope equipped with a camera, sometimes referred to as high-efficiency photon detection system. Suitable photon detection systems include, but are not limited to, photodiodes and intensified CCD cameras.

In one embodiment, examples of techniques suitable for single molecule detection of the spectral properties of probes include confocal laser (scanning) microscopy, wide-field microscopy, near-field microscopy, fluorescence lifetime imaging microscopy, fluorescence correlation spectroscopy, fluorescence intensity distribution analysis, measuring brightness changes induced by quenching/dequenching of fluorescence, or fluorescence energy transfer.

In a further aspect of the disclosure, the N-terminal amino acid of the polypeptide is cleaved. Cleaving exposes the N-terminal amino group of an adjacent (penultimate) amino acid on the polypeptide, whereby the adjacent amino acid is available for reaction with a new probe. Optionally, the polypeptide is sequentially cleaved until the last amino acid in the polypeptide (C-terminal amino acid).

In one embodiment, sequential chemical degradation is used to cleave the N-terminal amino acid of the polypeptide. Edman degradation generally comprises two steps, a coupling step and a cleaving step. These steps may be iteratively repeated, each time removing the exposed N-terminal amino acid residue of a polypeptide. In one embodiment Edman degradation proceeds by way of contacting the polypeptide with a suitable Edman reagent such as PITC, or a ITC-containing analogue, at an elevated pH to form a N-terminal thiocarbamyl derivative. Reducing the pH, such by the addition of trifluoroacetic acid results in the cleaving the N-terminal amino acid thiocarbamyl derivative from the polypeptide to form a free anilinothiozolinone (ATZ) derivative. Optionally, this ATZ derivative may be washed away from the sample. In one embodiment the pH of the sample is modulated in order to control the reactions governing the coupling and cleaving steps.

In some embodiments, the N-terminal amino acid is contacted with a suitable Edman reagent such as PITC, or an ITC containing analogue, at an elevated pH prior to contacting the affixed polypeptide with a plurality of probes that selectively bind the N-terminal amino acid derivative. Optionally, the cleaving step comprises reducing the pH in order to cleave the N-terminal amino acid derivative.

In one embodiment of the description, the method includes comparing the sequence obtained for each polypeptide molecule to a reference protein sequence database. In some embodiments, small fragments comprising 10-20, or fewer, sequenced amino acid residues, consecutive or with gaps, may be useful for detecting the identity of a polypeptide in a sample.

The following examples illustrate embodiments of the invention and are not intended to limit the scope of the invention.

Example 1: Single Molecule Spectroscopy-Based Amino Acid Residue Identification

The inventor has adapted super-resolution fluorescence microscopy to an Edman-like sequencing process, allowing for the simultaneous, massively parallel identification and counting of large numbers of individual protein molecules. The protein molecules may be in vitro or in situ such as in cells and/or tissues. N-terminal amino acid residues of affixed polypeptides are reacted with a fluorescent probe that confers distinct spectral properties upon coupling to different amino acids. The resulting characteristic emission profile generated by the distinct N-terminal derivative formed on individual protein molecules is monitored by super-resolution spectroscopy to determine the identity of the corresponding cognate amino acid residue, which is then cleaved off, such as through Edman-like chemistry. Through multiple, iterative cyclic rounds of coupling the remaining polypeptide portions to fresh dye, re-imaging the population of N-terminal probes, followed by selective cleavage of consecutive probe derivatives, partial sequence and precise localization information is obtained for thousands to millions of protein molecules imaged in a concurrent manner. Given access to genomic information, the probe used for imaging need not resolve all of the amino acid side chains, but rather just a sufficient subset, in series or with gaps, in order to unambiguously identify all of the protein molecules present in a biological sample.

Fluorescence refers to the ability of certain molecules, such as organic dyes, to absorb light at a particular wavelength and, after a brief interval, emit light at a different (longer) wavelength. Fluorescence properties that can be precisely measured include emission intensity, polarity/anisotropy, and lifetime. To detect a particular protein target, fluorophores are usually covalently coupled to an antibody. Due to diffraction of the dye emission wave, the smallest features normally resolvable by microscopy are ~250 nm in the lateral (x-y) plane. Overlapping concurrent emissions from adjacent probes usually obscures smaller features, preventing determination of individual components present in structures like the cell membrane, nucleus or cytoskeleton, or multiprotein complexes. However, super-resolution imaging techniques, allow for the precise localization of individual fluorescently labeled protein molecules. Methods like STORM achieve sub-diffraction resolution by spatially and temporally separating the fluorescence emission of individual fluorophores through reversible, stochastic transitioning of only a small fraction from a dark (off) state to a bright (on) state, such that only one molecule is detected per diffraction-limited area. Using ultrasensitive digital cameras to detect these transient low intensity signals at high speed, the imaging process is repeated until all probes present in a field of view are detected sequentially, typically over 10,000+ frames that are each populated with a sparse subset of dye emissions. Individual molecules are then precisely localized using software to fit centroids over each signal, from which a final super-resolution image is reconstructed. While compatible with live cell or 3D imaging, single molecule imaging currently requires highly selective probes (e.g. antibodies), and only limited target multiplexing (simultaneous detection of different proteins) has been achieved.

The inventor has determined that characteristic changes in the properties of certain fluorescent dyes occur when covalently bound to different amino acids.

For example, high yield xanthene dyes that predominate as dark spirocyclic structures (eg. rhodamine lactone) but reversibly open to restore fluorescence are ideally suited to single molecule sequencing. Photoswitching is usually controlled by experimental conditions (eg. using thiols, irradiation intensity, pH), but Uno et al. (*Nat Chem.* 2014 August; 6(8):681-9) recently reported xanthene-based dyes that blink spontaneously.

Figure 1:
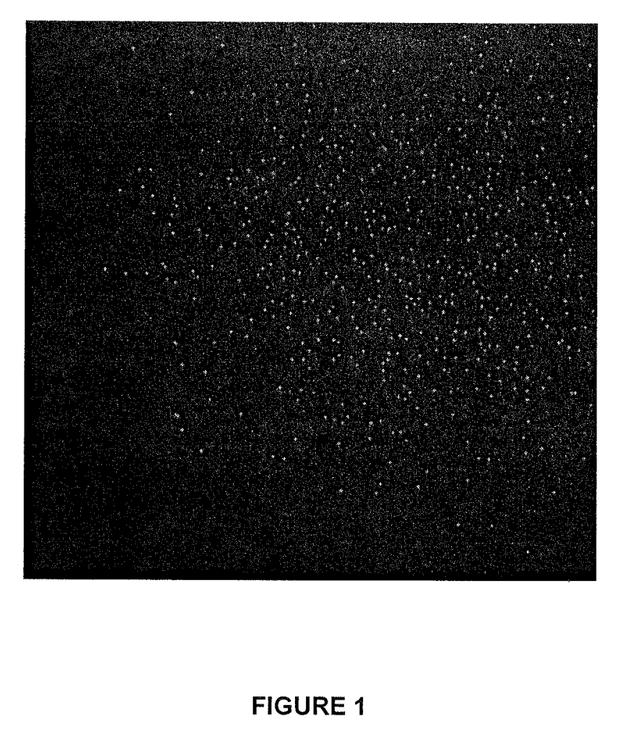
FIG. 1 shows a representative frame of the single molecule imaging (STORM) of HMRG coupled, via an ITC moiety, to Immunoglobulin (IgG). The number of localizations recorded per 1000 frames was 573,052. The average fluorescent intensity measured per individual molecule was 9111.153 and the average location uncertainty was 18.39 nm.

As shown in FIG. 1 by synthesizing a reactive isothiocyanate group onto a blinking dye (to confer Edman-like degradation), the inventor has determined that it is possible to (i) efficiently label the N-terminals of individual polypeptide molecules, (ii) detect fluorescent emission and blinking by single molecule imaging, and (iii) selectively cleave off the conjugated N-terminal residue, revealing the next (penultimate) amino acid. The inventor also determined that since the emission profile (intensity, wavelength shape, other spectral properties) of some dyes is influenced by the local chemical (electron donating/extracting) environment, small, but characteristic, changes in emission properties (such as a reproducible shift in wavelength profile) formed after conjugation to different amino acids can be used to infer the identity of the corresponding labeled N-terminal residue. By repeating the labeling, imaging, and degradation process in an iterative manner, the identity (partial sequence) and abundance (occurrences) of large numbers of individual protein molecules may be determined simultaneously.

These methods and techniques may be used for the unbiased sequencing and counting of polypeptides, present either on a slide or flow cell, or at the plasma membrane or within intracellular organelles of a cell, thereby revealing the composition, localization and physical interactions of proteins that are present.

After covalent coupling of the probe to the N-terminal, an "optical signature" unique to one or more particular cognate amino acids is identified. The underlying rationale is that atomic interactions, differentially induced by adjacent amino acid side chains, affect the electronic states and hence ground and excited states of the dye differently, leading to subtle, but reproducible, variations in emission intensity, polarity, or peak shape. The spectral profiles of individual fluorescent dye molecules using a wide-field imaging method (for example, spectrally resolved stochastic optical reconstruction microscopy, SR-STORM; see e.g. Zhang et al. *Nat Methods.* 2015 October; 12(10):935-8)) which can deconvolute small shifts in emission intensity or peak shape.

Remarkably, as shown in FIG. 2, the emission of certain rhodamine-derivatives is reproducibly altered in solution upon coupling to different amino acids ($\lambda^{emm}$~535 nm for Met vs. 524 nm for Trp).

Example 2: Identification and Characterization of Fluorescent Probes

Using fluorescent probes some, or all, of the 20+ naturally occurring amino acids may be distinguished by the detecting the fluorescent emission of the individual probes conjugated to different amino acids. Various dye molecules, such HMRG and other xanthene-derivatives, are investigated for their suitability as probes for single molecule spectroscopy-based residue identification.

Experiments are conducted in order to identify fluorescent probes suitable for distinguishing different amino acids and to define optimal imaging conditions (eg. buffer pH/polarity) that maximize discrimination, as well as the influence, if any, of adjacent amino acids (eg. penultimate residue). Large numbers of individual probe molecules are examined after immobilization to a surface (eg. coverslip, flowcell, or microbead), or natively in/on metazoan cells, microbes or virus, in order to derive a precise, imaging-based N-terminal readout for one, or more, optically-encoded fluorescent probes. To allow for iterative sequencing, the probe(s) may support N-terminal cleavage, such as through isothiocyanate-mediated degradation.

The surface of borosilicate coverglass is covered with proteins, either in a folded or denatured state, over a serially diluted concentration range (down to sub-ELISA detection limits). Analytes include synthetic peptides, polypeptides, and/or recombinant proteins, including antibodies, receptors, toxins, or enzymes; negative controls (no target or dye) are likewise assessed in parallel. Prior to exposure to the probe, reactive lysine side chains are chemically modified. To overcome native N-terminal blocks (eg. acetylation), which preclude sequence determination, proteases may be used to liberate a free amino group. After coupling to the probe, imaging is performed on a STORM-capable inverted total reflection fluorescence microscope, sampling multiple fields of view for statistical analysis. At 90× magnification, the surface area in each field of view is ~3600 $\mu m^2$, allowing hundreds of thousands of molecules to be imaged simultaneously.

For image analysis, ImageJ (available online from the National Institutes of Health, Bethesda, Md.) and other digital image processing software is used to process the image stacks of recorded probe emissions to identify individual fluorophores that blink and vanish. After correcting for lateral drift, probe locations (reporter coordinates and estimated uncertainty in nanometers) and differences in intensity and wavelength, or other emission properties, are calculated with sub-diffraction precision. Each optically-encoded reporter is individually classified by matching the emission profile to reference (standard) spectra to identify the cognate N-terminal amino acid. Spectral properties such as peak shape (maxima) and intensity, as fluorescent polarization/anisotropy and lifetimes will be measured. The probes are compared against well characterized antibodies labeled with standard STORM dyes (eg. Alexa647) in order to demonstrate highly selective target discrimination with exceptional quantitative accuracy and sensitivity.

Example 3: HMRG-BOC-ITC Coupling and Identifying Different N-Terminal Amino Acid by Fluorescence Profiling Materials and Methods Hydroxymethyl rhodamine green (HMRG) tert-butyloxycarbonyl (BOC) isothiocyanate (ITC) (HMRG-BOC-ITC) as shown in FIG. 4A was synthesized as shown in FIG. 4B and dissolved in DMSO to a final concentration 34 nmol/µl.

Peptide beads: Peptide beads were synthesized by Kinexus (Vancouver B.C). Tentagel resin (Tenta-Gel® M NH2, 10 µm beads, RAPP Polymer) was used as the support for solid peptide synthesis. The peptides were synthesized to have the amino acid sequence X-AGWYMRLG (SEQ ID NO: 1), where X represents any one of 20 different amino acids at N-termini of the peptide. Approximately half (~50%) of each peptide/resin contained a cleavable HMBA linker inserted between peptide sequence and the bead which enabled cleavage of the peptide molecules from the beads upon treatment with base.

Prior to coupling, 100 µl of dimethylformamide (DMF) was added to each tube containing dry peptide resin (~1.5-2 µmole of peptide). The bead slurry was stored at −20° C. and used as needed for coupling.

The coupling reaction contained the following:

5 µl of peptide bead slurry (75-100 nmol of peptide in DMF);
3.8 µl of HMRG-BOC-ITC in DMSO (129 nmol);
8.3 µl pyridine; and
3.6 µl dichloromethane (DCM).

As a non-peptide control, uncoupled tentagel resin not containing any peptide was treated with 2% acetic anhydride and 2% N,N-Diisopropylethylamine in DMF for at least 5 min in order to block free reactive NH2-groups. Solvents were evaporated and beads resuspended in DMF and used for coupling.

The coupling reaction was performed as follows. 5 µl of each of the peptide-bead slurry (75-100 nmol of peptide in DMF) and the blocked-beads slurry as a negative control (see below) was aliquoted into separate microcentrifuge tubes. A master mix containing 3.8 µl of dye HMRG-BOC-ITC (34 nmol/µl), 8.3 µl of pyridine and 3.6 µl of dichloromethane (DCM) was added to each tube. The tubes were incubated with gentle shaking in the dark overnight at 4° C.

For the non-peptide control, Tentagel resin (not containing any peptide) was treated with 2% acetic anhydride and 2% N,N-Diisopropylethylamine in DMF for at least 5 min in order to block free NH2-groups. Solvents were evaporated and the beads were resuspended in DMF and used as a control.

The next day coupled beads were washed extensively to remove uncoupled dye: 200 µl of DCM was added to each tube and the mixture transferred to 0.45 µm spin filter (UFC30HVNB, Amicon). After a short 30 second spin at 6000 rpm the flow-through was discarded and the beads retained on the filter was washed with the following solvents: DCM (2×), THF(tetrahydrofuran)(2×), and THF (20%)(4×), followed by short spins and discarding the flow-through. After washing, dry peptide resin was resuspended in 150 µl of 30% NH$_4$OH and transferred to a fresh tube. Tubes were incubated with gentle shaking at room temperature. After an incubation of 1-2 hours, the bead suspension (in NH$_4$OH) was transferred back to a spin filter and briefly centrifuged. The flowthrough, containing free cleaved-off peptides, was collected into a fresh tube and vacuum dried to remove the base. Dried peptides were resuspended in 150-200 µl of either of 10 mM phosphate buffer, pH7.4 containing 5% DMSO, or same buffer with 10% THF.

Fluorescence spectroscopic data of individual HMRG-BOC-coupled peptides was collected on a fluorometer (Fluorolog, Horiba) using 480 nm excitation light and emission profiles were acquired from 510 to 550 nm. The slit width of excitation and emission was 5 nm.

Results

The normalized intensity for each of the 20 different N-terminal conjugated HMRG-BOC-coupled peptides tested is shown in FIG. 5. The spectra exhibited different spectral signatures allowing for different N-terminal amino acids to be distinguished. For example, HMRG-BOC coupled to aspartic acid (D) exhibited a lower normalized intensity at higher wavelengths (540-550 nm) relative to other amino acids. HMRG-BOC coupled to N-terminal lysine (K) exhibited a lower normalized intensity at lower wavelengths (510-520 nm) relative to the other amino acids. HMRG-BOC coupled to N-terminal Asparagine (N) exhibited a distinctive increase in normalized intensity going from 540 nm to 550 nm.

Analysis of the spectra shown in FIG. 5 also indicated certain general trends in the spectral properties of the N-terminal amino acid-probe conjugates. As shown in FIG. 6, N-terminal amino acids that are hydrophobic such as Leucine tended to exhibit a red-shift in intensity relative to the average. N-terminal amino acids that are hydrophilic such as Aspartic acid tended to exhibit a blue-shift in intensity relative to the average.

By sequentially conjugating a fluorescent probe such as HMRG-BOC-ITC to the N-terminal amino acid of a polypeptide, obtaining a spectra of the probe-polypeptide conjugate, identifying the N-terminal amino acid of the polypeptide based on comparing the spectra to one or more reference spectra such as those shown in FIG. 5, and the cleaving the N-terminal amino acid of the polypeptide the sequence of the polypeptide may be determined.

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

All publications, patents and patent applications are herein incorporated by reference in their entirety to the same extent as if each individual publication, patent or patent application was specifically and individually indicated to be incorporated by reference in its entirety.

REFERENCES

Uno et al. *A spontaneously blinking fluorophore based on intramolecular spirocyclization for live-cell super-resolution imaging.* Nat Chem. 2014 August; 6(8):681-9

Zhang et al. *Ultrahigh-throughput single-molecule spectroscopy and spectrally resolved super-resolution microscopy.* Nature Methods 12, 935-938 (2015).

The invention claimed is:

1. A method of sequencing a polypeptide comprising:
   a) conjugating a probe to an N-terminal amino acid of the polypeptide wherein the probe exhibits different fluorescent spectral properties when conjugated to different N-terminal amino acids;
   b) detecting one or more fluorescent spectral properties of the probe conjugated to the N-terminal amino acid;
   c) identifying the corresponding N-terminal amino acid of the polypeptide by comparing the fluorescent spectral properties of the probe conjugated to the N-terminal amino acid of the polypeptide to a plurality of reference fluorescent spectral properties, wherein each reference fluorescent spectral property is representative of the probe conjugated to a different N-terminal amino acid;
   d) cleaving the N-terminal amino acid of the polypeptide; and
   e) sequentially repeating steps (a) to (d) with the same probe to determine the sequence of at least a portion of the polypeptide, wherein the sequence of the portion of the polypeptide comprises at least two different amino acids.

2. The method of claim 1, wherein the polypeptide is a single polypeptide molecule.

3. The method of claim 1, wherein the probe is covalently conjugated to the N-terminal amino acid of the polypeptide.

4. The method of claim 1, wherein detecting one or more fluorescent spectral properties comprises detecting fluorescence emission intensity, polarity/anisotropy or lifetime.

5. The method of claim 4, comprising detecting the fluorescence emission intensity, polarity/anisotropy or lifetime at a single wavelength or at a plurality of wavelengths.

6. The method of claim 1, wherein the probe comprises a xanthene derivative.

7. The method of claim 6, wherein the xanthene derivative is based on fluorescein, eosin, or rhodamine.

8. The method of claim 7, wherein the probe comprises a derivative of hydroxymethyl rhodamine green (HMRG).

9. The method of claim 1, wherein the probe comprises a spontaneously blinking dye or a photoswitchable dye.

10. The method of claim 1, wherein the probe comprises a reactive/labile isothiocyanate group.

11. The method of claim 10, wherein step d) comprises cleaving the N-terminal amino acid or N-terminal amino acid derivative of the polypeptide using Edman chemical degradation.

12. The method of claim 1, comprising sequencing a plurality of polypeptides in parallel wherein step a) comprises conjugating a plurality of probes to the N-terminal amino acid of each of the plurality of polypeptides, step b) comprises detecting one or more fluorescent spectral properties for each probe conjugated to the N-terminal amino acid of each of the plurality of polypeptides and step c) comprises identifying the N-terminal amino acid of each of the plurality of polypeptides by comparing the plurality of fluorescent spectral properties to the plurality of reference fluorescent spectral properties.

13. The method of claim 12, wherein the method comprises detecting one or more fluorescent spectral properties for each probe conjugated to the N-terminal amino acid of each of the plurality of polypeptides at spatially resolved locations in a sample containing the plurality of polypeptides.

14. The method of claim 1, wherein detecting one or more fluorescent spectral properties of the probe conjugated to the N-terminal amino acid comprises super resolution microscopy.

15. The method of claim 14, wherein the super resolution microscopy comprises stochastic optical reconstruction microscopy (STORM).

16. The method of claim 1, further comprising comparing the sequence of at least one polypeptide molecule determined in step e) to a reference protein sequence database.

17. The method of claim 1, wherein comparing the spectral properties of the probe to a plurality of reference spectral properties comprises the use of machine learning, genetic algorithms, or principle component analysis (PCA).

18. The method of claim 1, wherein step b) comprises obtaining a fluorescence emission spectra of the probe conjugated to the N-terminal amino acid and step c) comprising comparing the fluorescence emission spectra to a plurality of reference spectra, wherein each reference spectra is representative of the probe conjugated to a different N-terminal amino acid.

19. The method of claim 1, wherein the C-terminal end of the polypeptide is conjugated to a substrate.

20. The method of claim 19, wherein the C-terminal end of the polypeptide is conjugated to the substrate through a linker.

* * * * *